US009364387B2

(12) United States Patent
Hoefler (10) Patent No.: US 9,364,387 B2
(45) Date of Patent: Jun. 14, 2016

(54) ISOLATION CHAMBER WITH CELLULAR INFLUENCE SYSTEM

(76) Inventor: Craig Hoefler, Venice, CA (US)

(*) Notice: Subject to any disclaimer, the term of this patent is extended or adjusted under 35 U.S.C. 154(b) by 428 days.

(21) Appl. No.: 13/507,548

(22) Filed: Jul. 9, 2012

(65) Prior Publication Data

US 2014/0012068 A1 Jan. 9, 2014

(51) Int. Cl.
*A61H 23/02* (2006.01)
*A61M 21/00* (2006.01)
*A61H 33/04* (2006.01)
*A61H 33/00* (2006.01)

(52) U.S. Cl.
CPC .......... *A61H 23/0236* (2013.01); *A61H 33/04* (2013.01); *A61M 21/0094* (2013.01); *A61H 2033/0008* (2013.01); *A61H 2033/048* (2013.01); *A61H 2201/107* (2013.01); *A61H 2201/5035* (2013.01); *A61H 2201/5043* (2013.01); *A61H 2201/5058* (2013.01); *A61M 2021/005* (2013.01); *A61M 2021/0027* (2013.01); *A61M 2021/0066* (2013.01); *A61M 2205/3372* (2013.01); *A61M 2205/3375* (2013.01)

(58) Field of Classification Search
CPC ........... G09B 5/00; G09B 5/04; A61M 21/00; A61H 23/02; A61H 23/0236
USPC ................. 600/21, 26, 27; 434/432
See application file for complete search history.

(56) References Cited

U.S. PATENT DOCUMENTS

| 3,585,991 | A | * | 6/1971 | Balamuth | A61M 21/00 310/334 |
| 4,000,749 | A | * | 1/1977 | Busco | 600/21 |
| 4,216,766 | A | * | 8/1980 | Duykers et al. | 600/586 |
| 5,219,322 | A | * | 6/1993 | Weathers | 600/27 |
| 5,695,455 | A | * | 12/1997 | Alton et al. | 601/47 |
| 5,725,472 | A | * | 3/1998 | Weathers | 600/21 |
| 5,741,317 | A | * | 4/1998 | Ostrow | A61H 23/0245 607/81 |
| 6,488,617 | B1 | * | 12/2002 | Katz | 600/26 |
| 6,702,767 | B1 | * | 3/2004 | Douglas et al. | 601/15 |
| 6,974,425 | B2 | * | 12/2005 | Rogers et al. | 601/46 |
| 7,247,356 | B2 | * | 7/2007 | MacMaster | 428/1.2 |
| 7,578,783 | B2 | * | 8/2009 | Klein | 600/27 |
| 7,815,581 | B1 | * | 10/2010 | Sung | 601/2 |
| 8,517,911 | B1 | * | 8/2013 | Thompson | 600/27 |
| 2008/0125620 | A1 | * | 5/2008 | McNew | 600/27 |
| 2014/0174277 | A1 | * | 6/2014 | Mann | 84/331 |

OTHER PUBLICATIONS

Gary Robert Buchanan "Sona: Healing with Wave Front BIOresonance" (2008).*

* cited by examiner

*Primary Examiner* — Navin Natnithithadha
*Assistant Examiner* — Kaylee Wilson
(74) *Attorney, Agent, or Firm* — William J. Benman; Benman, Brown & Williams (57) ABSTRACT

A cellular influence system. The novel cellular influence system includes an isolation chamber, a solution disposed within the chamber for supporting a user in a state of floatation, and a source generator for applying cymatic frequencies to the user via the floatation solution. In an illustrative embodiment, the system is adapted to apply cymatic frequencies that stimulate activity in a specific region or regions of the brain to induce a higher state of consciousness capable of increased learning abilities, and a visual display unit designed to minimize splay such that the interior of the isolation chamber remains dark is provided within the chamber for delivering information to be learned to the user during the induced state. Optionally, the system may also include a neural monitor for measuring neural activity in the user and adaptively adjusting the cymatic frequencies applied to the user based on the measured activity.

13 Claims, 6 Drawing Sheets

Fig. 5

ISOLATION CHAMBER WITH CELLULAR INFLUENCE SYSTEM

BACKGROUND OF THE INVENTION

1. Field of the Invention

The present invention relates to isolation chambers. More specifically, the present invention relates to floatation tanks.

2. Description of the Related Art

An isolation chamber, or floatation tank, is a dark, sound-proofed enclosure containing a layer of salt water upon which a user floats. The chamber is typically designed to isolate the user from external stimuli such as light, sound, and, in particular, gravity. Epson salt is usually added to the water in the isolation tank to increase the density of the solution such that the user floats comfortably near the surface with the face above the water. The buoyancy created by this salt solution effectively eliminates the body's specific gravity, bringing the floater close to an experience of total weightlessness.

Isolation chambers are currently used primarily for relaxation or meditation purposes. However, floatation has the potential for more advanced applications. The sensory deprivation experienced during floating liberates the user's mind and body from many tasks that are typically performed continuously everyday such as processing sensory information and dealing with gravity. These liberated resources could then potentially be redirected for use in other activities such as learning or healing.

Conventional isolation chambers, however, are not equipped for promoting such activities and have no system for delivering information to the user. Isolation chambers typically do not include any audio/visual systems since they are designed to remove all external stimuli. Furthermore, a conventional audio system would sound "muddy" due to sound waves traveling through water (the user's ears are typically underwater while floating), and a conventional visual display would illuminate the chamber, eliminating the sensory deprivation effect desired in an isolation chamber.

Hence, a need exists in the art for an improved isolation chamber for redirecting a user's liberated resources to promote learning or healing.

SUMMARY OF THE INVENTION

The need in the art is addressed by the cellular influence system of the present invention. The novel cellular influence system includes an isolation chamber, a solution disposed within the chamber for supporting a user in a state of floatation, and a source generator for applying cymatic frequencies to the user via the floatation solution. In an illustrative embodiment, the system is adapted to apply cymatic frequencies that stimulate activity in a specific region or regions of the brain to induce a higher state of consciousness capable of increased learning abilities, and a visual display unit designed to minimize splay such that the interior of the isolation chamber remains dark is provided within the chamber for delivering information to be learned to the user during the induced state. Optionally, the system may also include a neural monitor for measuring neural activity in the user and adaptively adjusting the cymatic frequencies applied to the user based on the measured activity.

BRIEF DESCRIPTION OF THE DRAWINGS

FIG. 1b is a simplified diagram of the interior of the isolation chamber of FIG. 1a.

DESCRIPTION OF THE INVENTION

Illustrative embodiments and exemplary applications will now be described with reference to the accompanying drawings to disclose the advantageous teachings of the present invention.

While the present invention is described herein with reference to illustrative embodiments for particular applications, it should be understood that the invention is not limited thereto. Those having ordinary skill in the art and access to the teachings provided herein will recognize additional modifications, applications, and embodiments within the scope thereof and additional fields in which the present invention would be of significant utility.

The present invention provides a novel cellular influence system for manipulating various aspects of the human mind and body. The cellular influence system includes a hybrid isolation/floatation chamber that has been equipped with a variety of high-tech underwater audio devices and a sophisticated visual display unit. The platform is computer controlled and serves as an interface combining the human mind with computer intelligence to achieve a desired result in a multitude of areas.

The novel cellular influence system of the present invention operates by applying cymatic frequencies to a user floating in the isolation chamber. Cymatic therapy involves the application of sound waves to influence the body at a cellular level. Human cells, tissues, and organs are believed to each have a natural resonant frequency. Applying the appropriate frequency or combination of frequencies can therefore promote natural self-healing to maintain and possibly improve the body. Cymatic frequencies may also be used to affect neural activity in the brain.

Conventional cymatic therapy transmits cymatic frequencies to the body via sound waves through conventional speakers or headphones, typically traveling through air. In accordance with the present teachings, cymatic frequencies are transmitted to a user via a liquid crystal solution upon which the user is floating in the isolation chamber. The cymatic frequencies are thus transmitted by a liquid to liquid transference, through the floatation solution directly to the user's cells, which are primarily liquid. The underwater sound waves create geometric patterns in the floatation solution to which the user is exposed, causing the user's body to resonate at the applied frequencies and thereby producing cellular and systemic responses.

A predetermined sequence of frequencies is applied based on the specific objective to be achieved. Objectives can range from repairing physical injuries or diseased cells, to increasing mental capacity and elevating emotional states. In a preferred embodiment, cymatic frequencies are applied to increase activity in specific portions of the user's brain that elevate the user's mind to a higher state of consciousness capable of increased learning capacity, during which information from a computer may be imprinted to the user's mind through the audio/video system in the isolation chamber.

Figure 1A:
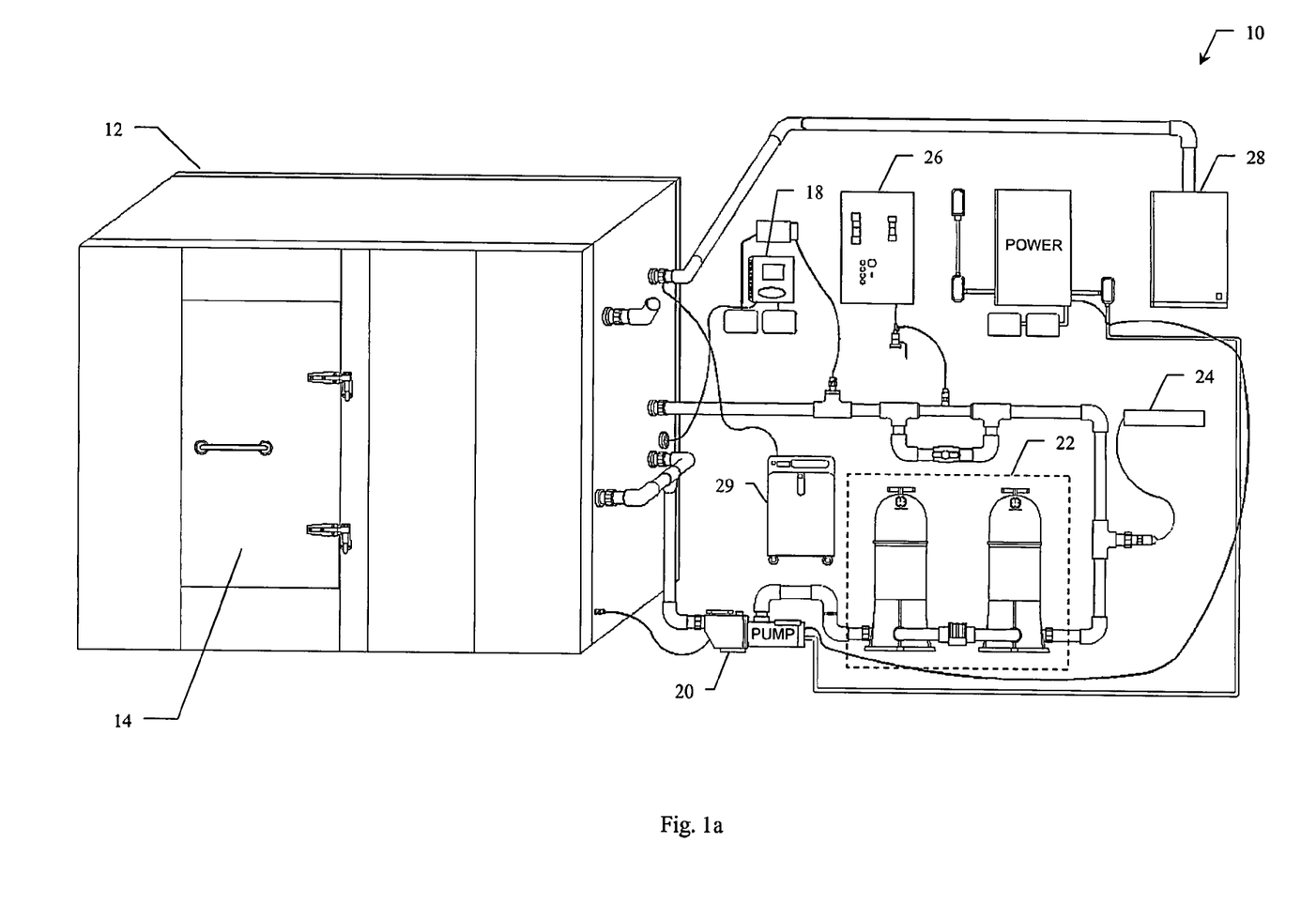
FIG. 1a is a simplified diagram of an isolation chamber designed in accordance with an illustrative embodiment of the present invention.
Figure 1B:
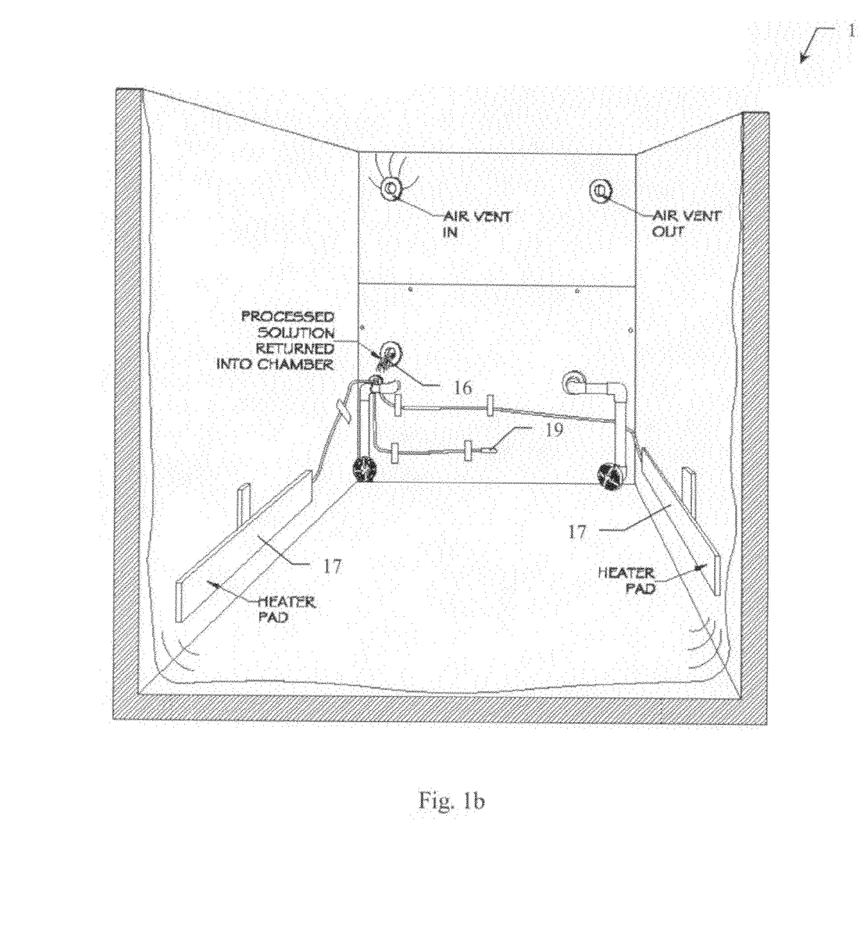
Figure 2:
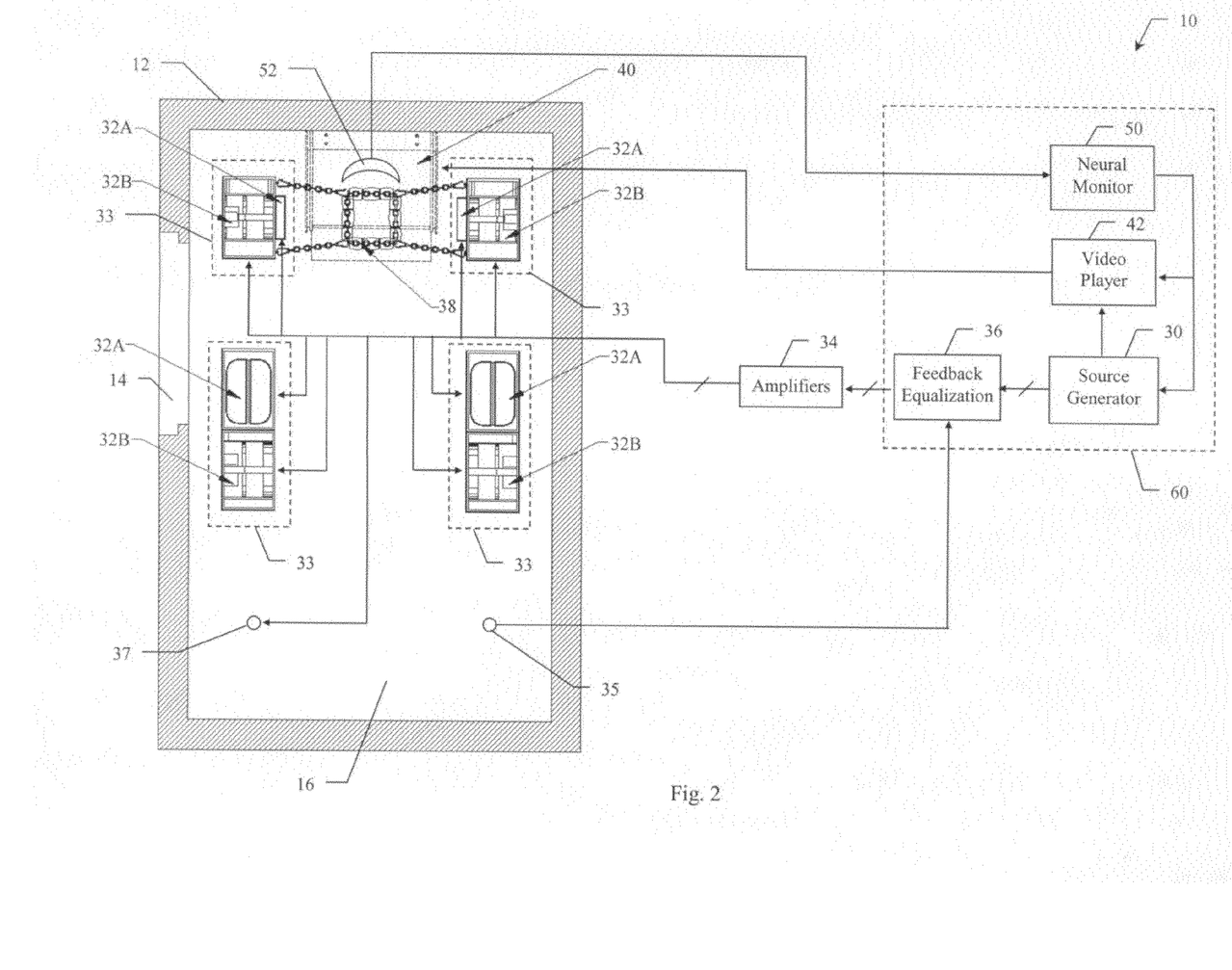
FIG. 2 is a simplified diagram showing a top view of the interior of the isolation chamber with a block diagram of a cellular influence system designed in accordance with an illustrative embodiment of the present invention.
Figure 3:
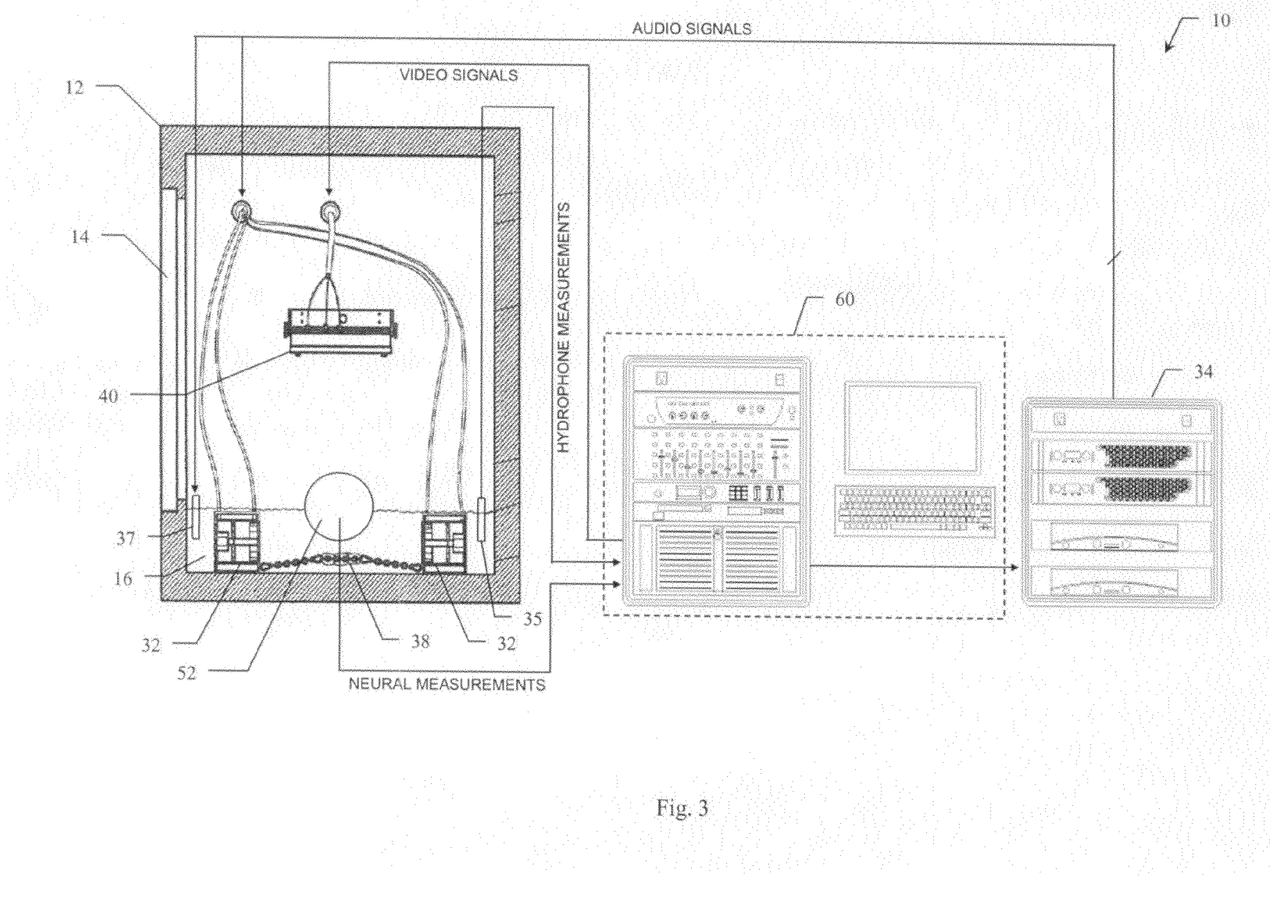
FIG. 3 is a simplified diagram showing a side view of the interior of an isolation chamber designed in accordance with an illustrative embodiment of the present invention.

FIG. 1a is a simplified diagram of the isolation chamber 12 of a cellular influence system 10 designed in accordance with an illustrative embodiment of the present invention, while FIG. 1b shows the interior of the isolation chamber 12. FIG. 2 is a simplified block diagram of the illustrative cellular influence system 10, showing a top view of the interior of the isolation chamber 12, while FIG. 3 shows a side view of the interior of the isolation chamber 12 and the external electronics.

As shown in FIGS. 1a and 1b, the cellular influence system 10 includes an isolation chamber 12, which is a lightless, soundproofed enclosure designed to provide a light- and sound-free environment therein. A door 14 provides access to the chamber 12. The chamber 12 contains a solution 16 having a specific gravity of about 1.27 to 1.3 for supporting a user in a state of floatation. In the illustrative embodiment, the chamber 12 contains a 12 inch deep, saturated solution 16 of Epsom salt (magnesium sulfate) in about 250 gallons of water (shown in FIG. 2). The chamber 12 includes heating pads 17 coupled to a heater controller 18 and sensor 19 for maintaining the temperature of the solution to match skin temperature (approximately 93.5° to 95°). The user floats in the chamber 12 in a dark, silent environment, with a feeling of weightlessness.

In a preferred embodiment, the system 10 includes circulation, filtration, and disinfection systems for cleaning the solution 16 between uses. As shown in FIG. 1a, the system 10 includes a pump 20 for circulating the solution 16, a double filtration system 22 with a 5 micron cartridge followed by a 0.5 micron cartridge, a UV disinfection system 24, and an ozone generating injection system 26 for cleaning the floatation solution 16. The entire environment within the chamber 12 is ventilated using an air purification unit 28 (such as an air purification unit designed for use in surgical clean rooms) in conjunction with an oxygen concentrator 29 to provide clean, disinfected, and oxygen-enriched air for the user to breathe while floating face-up in the salt solution 16.

In accordance with the present teachings, cymatic frequencies are transmitted to the user in the isolation chamber 12 via the liquid-crystal floatation solution 16. As shown in FIG. 2, the system 10 includes a source generator 30 coupled to a plurality of underwater speakers 32 submerged in the solution 16. The speakers 32 are powered by amplifiers 34 located outside of the chamber 12. In a preferred embodiment, the speakers 32 are held in place by weighted frames that can be repositioned as desired for each user. When the system is not in use, the speakers 32 can be removed from the solution 16 and stowed overhead. During operation, the speakers 32 are lowered into the solution 16 and positioned as desired around the user.

In the illustrative embodiment, the system 10 includes eight speakers 32, grouped into four speaker sets 33 placed around the user. Two speaker sets 33 are placed on either side of the user near the head, while the other two speaker sets 33 are placed on either side of the user near the center of the user's body. Each speaker set 33 may include multiple speakers 32. Current underwater speaker devices generally do not provide adequate clarity over the entire audible frequency range; they typically work well for only a narrow frequency band. The speaker sets 33 may therefore include multiple speakers 32 that together provide excellent frequency response over the entire audible spectrum. In the illustrative embodiment, each speaker set 33 includes two speakers 32: a first speaker 32A for providing good low to mid-range frequency response and a second speaker 32B for providing good high frequency response. Together, the speakers 32 thus provide a stereo, three-dimensional, spherical surround sound around the user.

The source generator 30 provides electrical signals containing the desired cymatic frequencies that are converted to sound waves by the underwater speakers 32. In the simplest embodiment, the source generator 30 may include an audio player that plays prerecorded audio tracks containing the cymatic frequencies. The source generator 30 may also include a synthesizer that synthesizes the desired frequencies. In a preferred embodiment, the source generator 30 includes software executed by a computer 60 for providing audio signals containing the desired cymatic frequencies based on a user selection.

The system 10 may also include a hydrophone 35 and a feedback equalization circuit 36 for adjusting the audio signals sent to the speakers 32 such that the signal received by the user after transmission through the liquid solution 16 is equal to the signal generated by the source generator 30. Environmental conditions, user movement, and properties of the speakers 32 and solution 16 could alter the transmitted signal by shifting frequencies, adding harmonic frequencies, attenuating some frequencies, etc. In accordance with the present teachings, a hydrophone 35 or other underwater audio sensor is placed in the solution 16 to measure the audio waves in the solution 16. A feedback equalization circuit 36 receives the monitored signals from the hydrophone 35 and automatically adjusts the signals sent to the amplifiers 34 and speakers 32 such that the received hydrophone signals are equal to the desired signals from the source generator 30. Thus, the equalization circuit 36 ensures that if the source generator 30 is transmitting a 1 kHz signal, for example, the user will receive a 1 kHz signal from the solution 16. In a preferred embodiment, the feedback equalization circuit 36 monitors and adjusts the transmitted signal continuously during operation. In the illustrative embodiment, the equalization circuit 36 is implemented in software executed by the computer 60.

The system 10 may also include one or more additional hydrophones 37 placed in the solution 16 for transmitting audio signals. Hydrophones can be used to both receive as well as transmit audio waves underwater. The system 10 may include a hydrophone 35 for receiving audio signals as discussed above and/or a hydrophone 37 for transmitting audio signals. The transmitting hydrophone 37 is added to the system to provide additional frequencies that may not be transmitted well by the speakers 32. In the illustrative embodiment, the speakers 32 and hydrophone 37 together provide a frequency range of about 1 Hz to 170 kHz.

In the preferred embodiment, the system 10 also includes a video display 40 and a video player 42 for providing visual stimuli to the user in the isolation chamber 12. In accordance with the present teachings, the video display 40 is specially designed to minimize splay from the display screen such that light output from the display 40 does not illuminate the interior of the isolation chamber 12. The user therefore sees only a floating image in an otherwise dark environment and the walls of the chamber 12 remain invisible. As shown in the illustrative embodiment of FIG. 4a, this is achieved by applying two layers of privacy coating on the display screen: a first privacy coating 44 for minimizing splay in a first direction (e.g., horizontal), and a second privacy coating 46 for minimizing splay in a second direction approximately perpendicular to the first direction (e.g., vertical). The two layers of privacy coating 44 and 46 should be offset by about five degrees to avoid any moiré patterns. "Vikuiti Advanced Light Control Film" by 3M is an example privacy coating that may be used for this purpose. This particular privacy coating includes a plurality of microlouvers that act like window blinds to control the direction of light transmission through the film such that the displayed image is visible on-axis but darkened from a side view. Thus, with two perpendicular layers of privacy coating, light output from the display is transmitted only straight down toward the user.

Figure 4A:
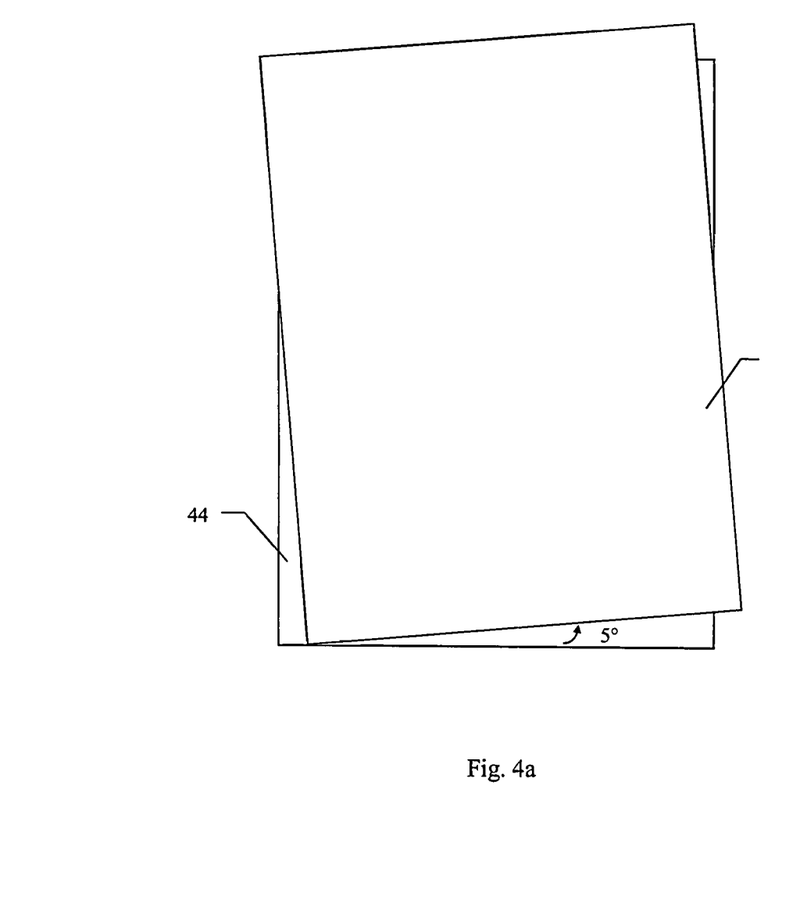
FIG. 4a is a simplified diagram showing the privacy films applied to the video display in accordance with an illustrative embodiment of the present invention.
Figure 4B:
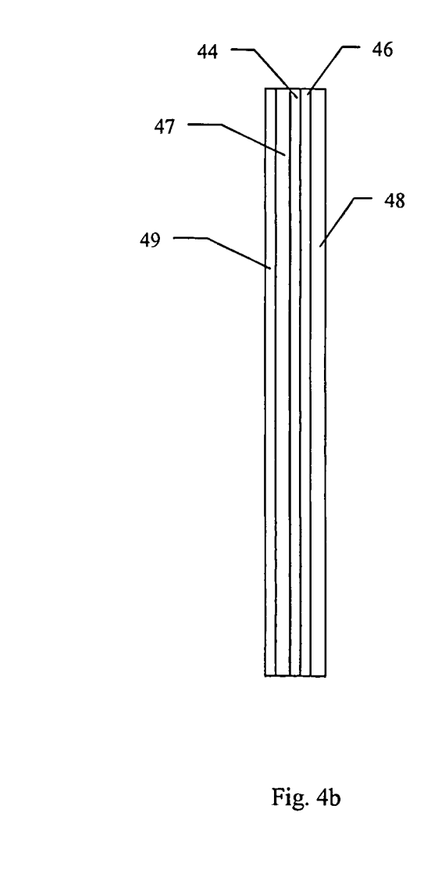
FIG. 4b is a side view of the films applied to the video display in accordance with an illustrative embodiment of the present invention.

FIG. 4b shows a side view of the films applied to the screen 40 in accordance with an illustrative embodiment of the present invention. The two layers of privacy film 44 and 46 are preferably sandwiched between two protective layers of polycarbonate 47 and 48. The video display 40 may also be coated with an anti-reflective film 49.

In an illustrative embodiment, the display 40 is an LED backlit LCD monitor, with the brightness levels dimmed to about 12-15% to minimize the amount of light output by the display 40 such that the user remains in a completely dark environment except for a floating image directly above him. Other monitors and types of privacy coating may also be used without departing from the scope of the present teachings.

The visual system 40, 42 may be used to deliver information to be learned by the user while in an enhanced learning state induced by the applied cymatic frequencies, or it may be used to provide visual stimuli for promoting the desired treatment. For example, the visual stimuli may include text containing predetermined words or phrases selected for accomplishing the desired goal, computer-generated graphics patterns or sequences illustrating visual representations of the applied cymatic frequencies, graphics representing cellular activity as a visualization aid during medicinal treatments, or video footage or still images of specific activities being performed correctly. The visual display 40 may also be used to extend the cymatic therapy concept by adding energy frequencies in the visible light range to the audio cymatic frequencies. The video player 42 can be programmed to display light of a specific frequency (color). Optionally, the source generator 30 may be adapted to provide a synchronized program of light and sound to address the desired objectives. In addition to light of a pure color, a program of images and/or videos can be created containing objects that are of a specific color.

The system 10 may also include a headrest 38 positioned underwater in the floatation solution 16 for supporting the user's head and helping to keep the user in a proper position between the underwater speakers 32 and directly beneath the visual display 40.

The cellular influence system 10 may also include a mechanism for measuring a response from the user while subject to the cymatic frequencies. For example, in a preferred embodiment, the cellular influence system 10 is used to apply cymatic frequencies that stimulate neural activity in particular portions of the user's brain. The system 10 may therefore include a mechanism for monitoring the user's neural activity. In the illustrative embodiment, the system 10 includes a neural monitor 50 and a waterproof monitoring cap 52 embedded with a plurality of EEG electrodes for measuring neural activity in the user. In a specific embodiment, the monitoring cap 52 includes 32 electrodes for measuring activity in 32 discrete locations of the brain. The neural monitor 50 may be implemented using specialized hardware or software running on a computer for receiving and analyzing the EEG measurements from the monitoring cap 52. Other types of monitoring devices for monitoring brain activity and/or other responses in other parts of the body may also be used depending on the desired treatment or objective.

The monitoring system 50 may be used during an experimental stage for determining which cymatic frequencies produce the desired responses. It may also be used during normal operation (treatment sessions) in a feedback system whereby the source generator 30 adjusts the frequencies being played based on the measurements received by the neural monitor 50 in order to maintain maximum desired activity in a particular region of the brain.

In an illustrative embodiment, the source generator 30, audio equalizers 36, video player 42, and neural monitor 50 are implemented in software executed by a computer 60 (shown in FIG. 3). Each system could also be implemented in separate, specialized hardware without departing from the scope of the present teachings.

Figure 5:
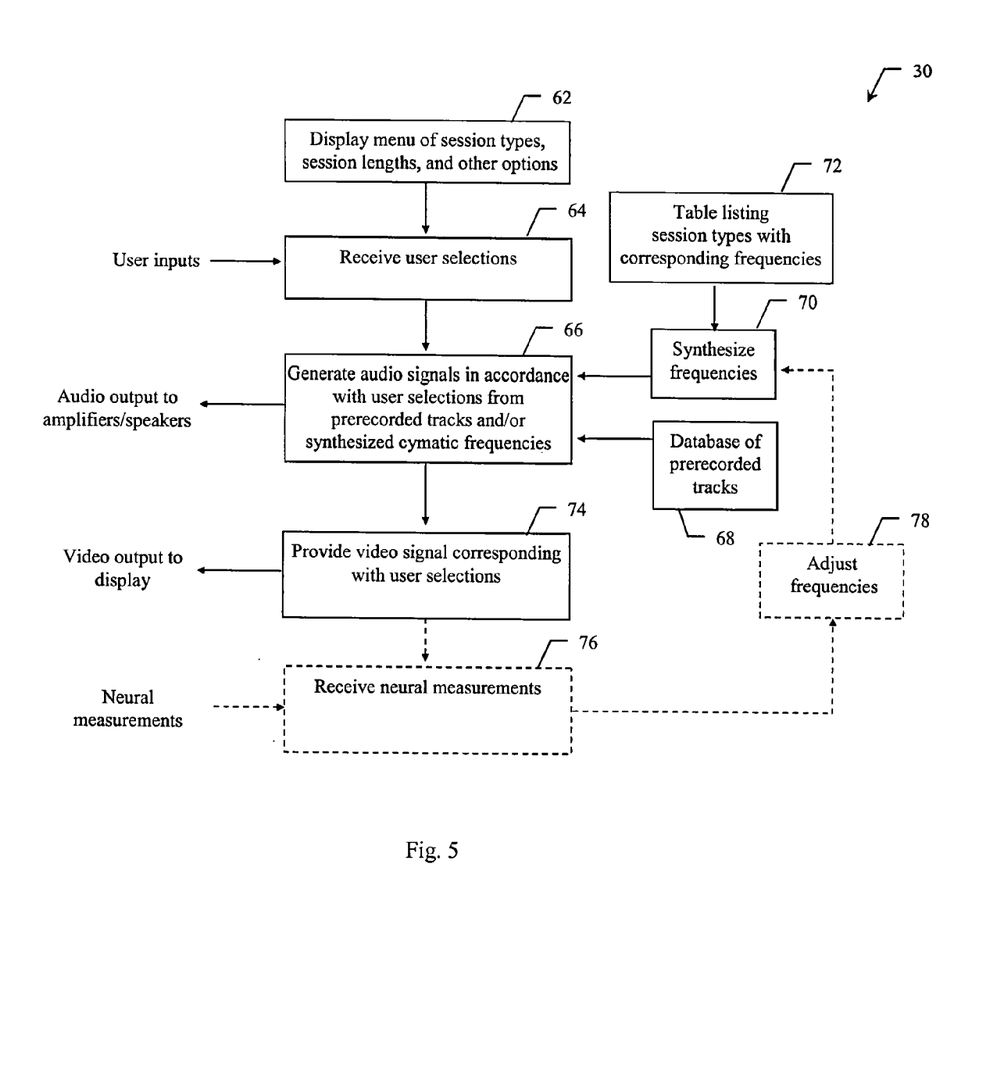
FIG. 5 is a simplified flow chart of a source generator designed in accordance with an illustrative embodiment of the present invention.

FIG. 5 is a simplified flow chart of a computer-implemented source generator 30 designed in accordance with an illustrative embodiment of the present invention. In the preferred embodiment, the source generator 30 is a software program running on a computer 60 that executes the following functions.

First, at Step 62, the program 30 displays a menu of session types (such as, for example, various sessions for learning, sessions for promoting healing of various organs, etc.) and any options available for each session (such as the length of the session). At Step 64, the program 30 receives the user's selections, and at Step 66, generates the appropriate audio signals based on the user selections to the underwater speakers 32. The audio signals may include selections from a database 68 of prerecorded tracks, and/or the audio signals may by synthesized by a synthesizer 70 using a table 72 that lists which frequency or frequencies correspond with which sessions.

In an illustrative embodiment, the shape of the programming in terms of amplitude, activity level, and intensity should be similar to that of a yoga class, including a commencement module, warm-up module, workout module, and cool-down module. At Step 66, the cymatic frequencies program 30 selects the appropriate modules based on the user selections.

If specified by the user's selection, at Step 74, the program 30 may provide a video signal for the video player 42 that contains desired visual stimuli such as a particular color for enhancing the effects of the cymatic frequencies, or information the user wishes to learn for a learning-type session.

If the system 10 is set up for feedback adjustments, at Step 76, the program 30 receives neural or other monitoring measurements from the neural monitor 50 and at Step 78, adjusts the frequencies delivered to the user (Step 70).

As an example, for an illustrative session having a total duration of ninety minutes, the session may include a commencement module of approximately ten minutes. This module involves a transition from regular consciousness to an elevated state of mind. At this starting phase, activity is minimal, movements are slow, and information is gradually introduced. This is a meditative and introspective phase that may involve a hypnotic technique of going to a mental location that is separate from the outside world, or of imagery walking down corridors and opening doors.

The warm-up module should be about fifteen minutes for an illustrative ninety-minute session. This module involves a slight increase in activity, gradually revealing the full dynamic range of volume and brightness, providing a general overall calibration of the mental and physical states. Cymatic frequencies are applied that accentuate alertness and a rise in physical mental energy level, preparing the individual for receiving information of the workout module.

The workout module lasts about sixty minutes. This module focuses on specific tasks and objectives. Cymatic frequencies, and optionally colors and movements, are directed at imprinting the desired material. Words, images, videos, and sounds provide information flow appropriate to the receptivity of the user. During this sequence, the intensity should start at medium and progress to the upper range, emphasizing repetition and focus.

Finally, the cool-down module of about five minutes should allow for a gradual decrease in activity followed by a free-floating period of time. It should be a mirror image of the hypnotic techniques used in the commencement module to access the mental workshop, returning the user to the outside world and to a waking consciousness.

In a preferred embodiment, the cellular influence system 10 is used to apply cymatic frequencies that stimulate neural activity in specific desired regions of the user's brain. Scientists have determined that different areas of the brain control different neural functions. For example, in general, the brainstem controls vital automatic functions such as breathing, heart rate, blood pressure, and consciousness; the cerebellum controls movement and muscle coordination; the frontal lobe is associated with reasoning, conscious thought, and higher cognitive functions; the parietal lobe is associated with processing sensory information such as pressure, touch, and pain; the temporal lobe processes smell and sound; and the occipital lobe processes visual stimuli.

The cellular influence system 10 is designed to stimulate activity in a specific region or regions of the brain (for example, to induce a higher state of consciousness capable of increased learning abilities) while minimizing activity in other regions such that more of the body's resources can be focused on the desired objective (e.g., learning). The sensory deprivation environment provided by the floatation chamber 12 minimizes brain activity by eliminating background sound and visual stimuli. Floating achieves a feeling of weightlessness, effectively eliminating the effect of gravity, which has been estimated to occupy 90% of all central nervous system activity. By freeing the brain from gravity and other external stimuli, floating liberates vast amounts of resources and large areas of the brain which can then be redirected toward the desired treatment or activity.

This redirection is accomplished by applying cymatic frequencies to the user to stimulate a particular region or regions of the brain (or to stimulate healing in a particular part of the body) as desired. In operation, during a first experimental stage, research will be conducted to determine which regions of the brain are stimulated by which frequencies. In the illustrative embodiment, different frequencies and combinations of frequencies are generated by the cymatic frequencies generator 30 and applied to the user in the floatation chamber 12. The neural monitor 50 then measures and records the user's neural responses to the cymatic frequency stimuli. A table 72 can then be generated listing which frequency or frequencies should be applied to stimulate each desired region of the brain. Experiments may also be conducted to determine if visual stimuli, such as displaying certain colors via the visual display 40, in combination with the cymatic audio frequencies can help to increase the desired response.

In an illustrative application, the cellular influence system 10 is used for learning. Cymatic frequencies shown to stimulate regions of the brain that induce a higher state of consciousness capable of increased learning abilities are applied to a user in the floatation chamber 12. Information that the user wishes to learn is then transmitted to the user via the visual display 40 and/or underwater speakers 32 (the source generator 30 may be adapted to mix any audio information with the cymatic frequencies for transmission through the speakers 32). The floatation chamber 12 in combination with the application of the appropriate cymatic frequencies helps the user to learn and retain information (such as learning a musical instrument, for example) provided by the computer 60.

Similarly, the cellular influence system 10 may be used to help athletes improve performance by visually imprinting muscle memory. Frequencies experimentally determined to improve this type of imprinting are applied to the user via the floatation chamber. Images showing the correct way to perform an athletic move are then repeatedly shown to the user via the display 40. For example, the video player 42 may display a sequence of still images showing a perfect golf swing.

As another example, the cellular influence system 10 may be used to simulate a particular response, such as simulating the neurological effect of a drug for rehabilitation purposes. Experiments can be conducted to determine which frequencies stimulate the regions of the brain that are activated during drug use. During rehabilitation, these frequencies are applied to a patient to mimic the effects of the drug and gradually reduce the stimulated activity to wean the patient off the drug without any chemicals.

Thus, the cellular influence system of the present invention can be used for a variety of applications. In general, experiments are conducted to determine which cymatic frequencies will stimulate a desired response. In operation, the user floats in the isolation chamber to liberate the mind and body's resources by minimizing the effects of gravity and external stimuli. The desired cymatic frequencies are then applied to the user via a liquid-to-liquid transference through the floatation solution. Any desired learning material or treatments can then be delivered to the user via the visual display and/or underwater speakers.

Thus, the present invention has been described herein with reference to a particular embodiment for a particular application. Those having ordinary skill in the art and access to the present teachings will recognize additional modifications, applications and embodiments within the scope thereof. For example, instead of direct immersion in a liquid, a waterbed may be provided to support the user. The cymatic frequencies are then applied to the user via the liquid in the waterbed either through internally mounted hydrophones or externally mounted speakers. Further, a control mechanism may be provided within the chamber to enable the user to adjust the amplitude, frequency, shape and location of the cymatic signal while inside the chamber. In addition, the in-chamber display may be implemented with a free-space display such as an optical light projector adapted to project light onto a liquid spray or vapor surface. As an alternative, the images may be projected onto the walls of the chamber.

It is therefore intended by the appended claims to cover any and all such applications, modifications and embodiments within the scope of the present invention.

Accordingly,

What is claimed is:

1. A cellular influence system comprising:
    an isolation chamber;
    a solution disposed within said chamber for supporting a user in a state of floatation;
    first means for applying to said user specific vibrational frequencies via said solution, said first means further including a plurality of underwater speakers submerged within said solution and positioned to surround the user with said vibrational frequencies in stereo, three-dimensional, spherical manner and a source generator for providing to said speakers audio signals to generate said vibrational frequencies; and feedback means for adjusting the vibrational frequencies applied to said user via said solution to resonate with said user and thereby optimize influence of said vibrational frequencies on said user on a cellular level, said feedback means including:

a hydrophone for measuring vibrational frequencies in said solution and a feedback equalization circuit configured to compensate for frequency shift, harmonics and attenuation of the vibrational frequencies applied to the user due to environmental conditions, user movement, speaker properties and said solution by adjusting said audio signals sent to said speakers based on said measured vibrational frequencies in said solution and a desired vibrational frequency to be received by said user.

2. The invention of claim 1 wherein said system further includes second means for providing visual stimuli to said user.

3. The invention of claim 2 wherein said second means includes a display unit having third means for minimizing splay such that energy emitted from said display unit does not illuminate said chamber.

4. The invention of claim 3 wherein said third means includes two layers of privacy coating disposed over said display unit, said two layers including a first layer oriented in a first direction and a second layer oriented in a second direction approximately perpendicular to said first direction.

5. The invention of claim 2 wherein said visual stimuli includes information to be learned by said user.

6. The invention of claim 2 wherein said visual stimuli includes specific colors for enhancing an effect of said vibrational frequencies.

7. The invention of claim 1 wherein said feedback means further includes means for measuring a response of said user to said vibrational frequencies.

8. The invention of claim 7 wherein said means for measuring a response of said user to said vibrational frequencies includes a neural monitor for measuring neural activity in said user.

9. The invention of claim 8 wherein said means for measuring a response of said user to said vibrational frequencies includes a monitoring cap embedded with a plurality of EEG electrodes.

10. The invention of claim 8 wherein said feedback means further includes means for adjusting said vibrational frequencies based on said measured response.

11. The invention of claim 1 wherein said system is adapted to apply vibrational frequencies that stimulate activity in a specific region or regions of the brain.

12. The invention of claim 11 wherein said system is adapted to apply vibrational frequencies that stimulate activity in a specific region or regions of the brain to induce a higher state of consciousness capable of increased learning abilities.

13. A cellular influence system comprising:

an isolation chamber;

a solution disposed within said chamber for supporting a user in a state of floatation;

a plurality of underwater transducers submerged within said solution for applying vibrational frequencies to said user via said solution in stereo, three-dimensional, spherical manner; and a feedback mechanism for adjusting the vibrational frequencies applied to said user via said solution to optimize influence of said vibrational frequencies on said user on a cellular level, said feedback mechanism including:

a hydrophone for measuring vibrational frequencies in said solution, and a feedback equalization circuit, coupled to said hydrophone, configured to compensate for frequency shift, harmonics and attenuation of the vibrational frequencies applied to the user due to environmental conditions, user movement, speaker properties and said solution by adjusting said audio signals sent to said speakers based on said measured vibrational frequencies in said solution and a desired vibrational frequency to be received by said user.

* * * * *